United States Patent
Tang et al.

(10) Patent No.: US 11,830,981 B2
(45) Date of Patent: Nov. 28, 2023

(54) ELECTROLYTE AND ELECTROCHEMICAL DEVICE

(71) Applicant: NINGDE AMPEREX TECHNOLOGY LIMITED, Ningde (CN)

(72) Inventors: Chao Tang, Ningde (CN); Jianming Zheng, Ningde (CN)

(73) Assignee: NINGDE AMPEREX TECHNOLOGY LIMITED, Ningde (CN)

( * ) Notice: Subject to any disclaimer, the term of this patent is extended or adjusted under 35 U.S.C. 154(b) by 807 days.

(21) Appl. No.: 16/961,826

(22) PCT Filed: Dec. 26, 2019

(86) PCT No.: PCT/CN2019/128847
§ 371 (c)(1),
(2) Date: Jul. 13, 2020

(87) PCT Pub. No.: WO2021/128203
PCT Pub. Date: Jul. 1, 2021

(65) Prior Publication Data
US 2021/0408602 A1 Dec. 30, 2021

(51) Int. Cl.
| | |
|---|---|
| *H01M 10/0568* | (2010.01) |
| *H01M 50/417* | (2021.01) |
| *H01M 50/449* | (2021.01) |
| *H01M 10/0567* | (2010.01) |
| *H01M 10/0569* | (2010.01) |
| *C07C 255/05* | (2006.01) |
| *H01M 4/36* | (2006.01) |
| *H01M 4/38* | (2006.01) |
| *H01M 4/48* | (2010.01) *C07D 327/00* |
| (2006.01) | *C07D 327/06* |
| (2006.01) | |

(52) U.S. Cl.
CPC ....... *H01M 10/0568* (2013.01); *C07C 255/05* (2013.01); *C07D 327/00* (2013.01); *H01M 4/366* (2013.01); *H01M 4/386* (2013.01); *H01M 4/48* (2013.01); *H01M 10/0567* (2013.01); *H01M 10/0569* (2013.01); *H01M 50/417* (2021.01); *H01M 50/449* (2021.01); *H01M 2300/0025* (2013.01)

(58) Field of Classification Search
CPC .......... H01M 10/0568; H01M 50/417; H01M 50/449; H01M 4/366; H01M 4/386; H01M 4/48; H01M 10/0567; H01M 10/0569; H01M 2300/0025; C07C 255/05; C07D 327/06
See application file for complete search history.

(56) References Cited

FOREIGN PATENT DOCUMENTS

| CN | 103682416 A | 3/2014 |
|---|---|---|
| CN | 104766995 A | 7/2015 |
| CN | 104900916 A | 9/2015 |
| CN | 106602141 A | 4/2017 |
| CN | 107749493 A | 3/2018 |
| CN | 106602141 B | 1/2019 |
| CN | 109786835 A | 5/2019 |
| CN | 109860703 A | 6/2019 |

(Continued)

OTHER PUBLICATIONS

International Search Report, dated Jul. 29, 2020, in counterpart PCT application PCT/CN2019/128847, 5 pages.

(Continued)

*Primary Examiner* — Brian R Ohara
*Assistant Examiner* — Patrick Marshall Greene
(74) *Attorney, Agent, or Firm* — Juan Carlos A. Marquez; Marquez IP Law Office, PLLC

(57) ABSTRACT

An electrolyte, including: a compound of Formula I, and at least one of a compound of Formula II or a compound of Formula III, Formula I Formula II Formula III $R_1$, $R_2$, $R_3$ and $R_4$ are each independently selected from hydrogen, fluoro, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, substituted or unsubstituted $C_6$-$C_{12}$ aryl, substituted or unsubstituted $C_1$-$C_{10}$ alkoxy, or substituted or unsubstituted $C_6$-$C_{12}$ aryloxy, wherein when substituted, the substituent is fluoro, cyano or $C_1$-$C_{10}$ alkyl; and a, d and f are each independently selected from an integer from 1 to 5, and b, c, e, g, h and i are each independently selected from an integer from 0 to 5.

20 Claims, No Drawings

(56) References Cited

FOREIGN PATENT DOCUMENTS

| | | |
|---|---|---|
| CN | 110165219 A | 8/2019 |
| CN | 110265608 A | 9/2019 |
| WO | 2018179883 A1 | 10/2018 |

OTHER PUBLICATIONS

Chinese First Office Action and Search Report, dated Nov. 3, 2021, in counterpart Chinese application CN201980021990.8, 9 pages in Chinese.

ELECTROLYTE AND ELECTROCHEMICAL DEVICE

CROSS REFERENCE TO THE RELATED APPLICATIONS

The present application is a National Stage application of PCT international application: PCT/CN2019/128847, filed on 26 Dec. 2019, the disclosure of which is hereby incorporated by reference in its entirety.

TECHNICAL FIELD

The present application relates to the technical field of energy storage technologies, and more particularly to an electrolyte and an electrochemical device containing the electrolyte.

DESCRIPTION OF RELATED ART

Lithium-ion batteries have the advantages of high energy density, high working voltage, low self-discharge rate, long cycle life, and causing no pollution, and are currently widely used as a power source in electronic products such as cameras, mobile phones, drones, notebook computers, smart watches and so on. In recent years, with the rapid development of smart electronic products, the requirements for the life of lithium-ion batteries have been raised. Increasing the charging cut-off voltage of lithium-ion batteries and enhancing the deintercalation of lithium from the positive electrode materials are effective means to improve the energy density of lithium-ion batteries. At present, high-voltage lithium-ion battery products of 4.4 V have been widely used, and a high-voltage system that further increases the charging cut-off voltage to 4.45V or even to a value higher than 4.5V is a hot spot in the research by major scientific research units and battery manufacturers. However, increasing the charging cut-off voltage will also bring many problems, for example, the battery gets prone to bulging, and the cycle capacity declines rapidly at high temperature etc. How to solve the problems associated with the high-energy density and high-voltage lithium-ion battery to improve the battery life has become an important subject in the field.

SUMMARY

The present application provides an electrolyte and an electrochemical device including the electrolyte. The electrolyte includes a substituted or unsubstituted thiodilycolic anhydride, and a trinitrile compound. The electrolyte can form a stable SEI protective layer on positive and negative electrodes, can significantly improve cycle performance at high temperature, especially high-temperature intermittent cycle performance, and suppress gas generation in discharge state.

An aspect of the present application provides an electrolyte. In some embodiments, the electrolyte includes
a compound of Formula I; and
at least one of a compound of Formula II or a compound of Formula III;

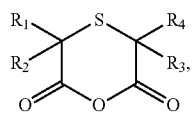

Formula I

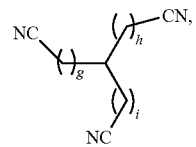

Formula II

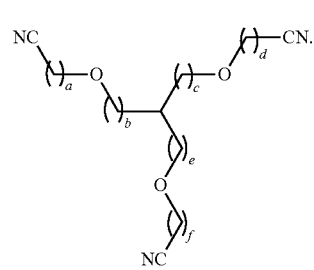

Formula III wherein $R_1$, $R_2$, $R_3$ and $R_4$ are each independently selected from hydrogen, fluoro, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, substituted or unsubstituted $C_6$-$C_{12}$ aryl, substituted or unsubstituted $C_1$-$C_{10}$ alkoxy, or substituted or unsubstituted $C_6$-$C_{12}$ aryloxy, wherein when substituted, the substituent is fluoro, cyano or $C_1$-$C_{10}$ alkyl; and a, d and f are each independently selected from an integer from 1 to 5, and b, c, e, g, h and i are each independently selected from an integer from 0 to 5.

In some embodiments, the compound of Formula I includes at least one of

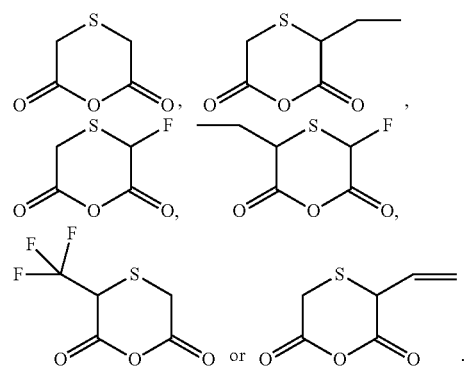

In some embodiments, the compound of Formula I accounts for 0.05 wt % to 3 wt % based on the weight of the electrolyte.

In some embodiments, the compounds of Formula II and Formula III include at least one of

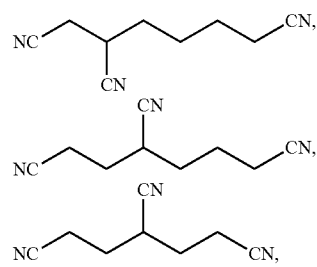

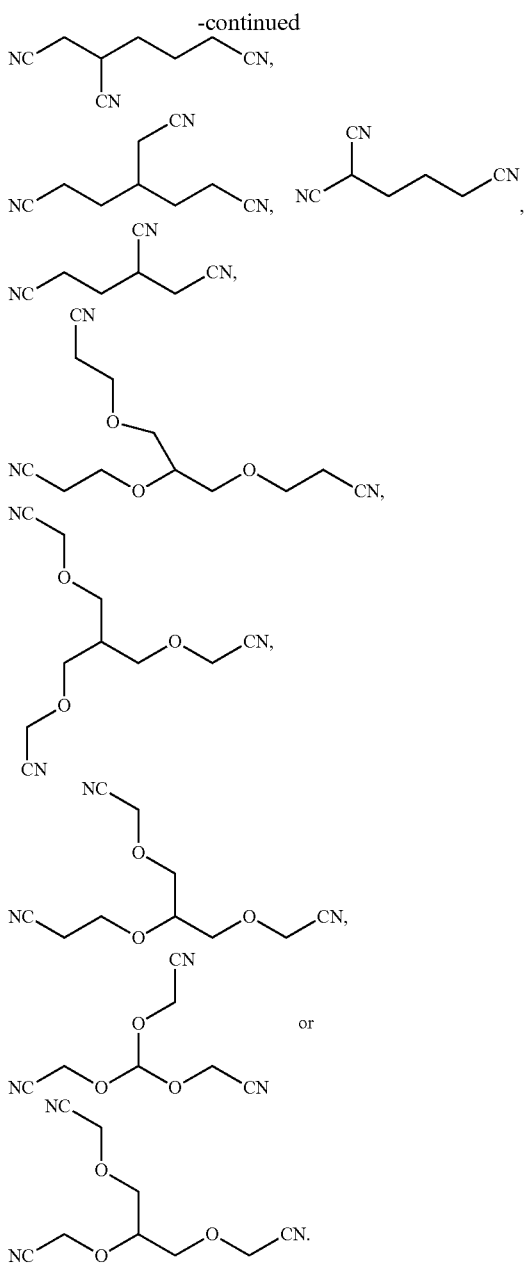

In some embodiments, the compound of Formula II, the compound of Formula III, or a combination thereof accounts for 0.1 wt % to 5 wt % based on the weight of the electrolyte.

In some embodiments, the electrolyte further includes an additive A, which includes at least one of lithium difluoro(oxalato)borate, lithium bis(oxalato)borate, lithium tetrafluoroborate, lithium difluorophosphate, lithium tetrafluorophosphate, lithium tetrafluoro(oxalato)phosphate, lithium difluorobis(oxalato)phosphate, sodium bis(fluorosulfonyl)imide, sodium bis(trifluoromethanesulfonyl)imide, sodium hexafluorophosphate, potassium bis(fluorosulfonyl)imide, potassium bis(trifluoromethanesulfonyl)imide or potassium hexafluorophosphate.

In some embodiments, the additive A accounts for about 0.01 wt % to about 1 wt % based on the weight of the electrolyte.

Another aspect of the present application provides an electrochemical device. The electrochemical device includes a positive electrode, a negative electrode, a separator film, and any electrolyte as described above.

In some embodiments, the separator film in the electrochemical device includes a polyolefin layer with a coating on the surface, wherein the coating includes a metal oxide $Me_xO_y$, wherein Me is at least one selected from Al, Mg, Zn, Ti or Zr, $1 \leq x \leq 2$, and $1 \leq y \leq 3$; and the thickness of the coating is about 0.1 micron to about 3 microns.

In some embodiments, the ratio of the thickness of the coating in the electrochemical device to the thickness of the polyolefin layer is about 1:1 to about 1:20.

In some embodiments, the metal oxide includes at least one of $Al_2O_3$, ZnO, $SiO_2$, MgO, $TiO_2$ or $ZrO_2$.

In some embodiments, the negative electrode includes a silicon-containing material, wherein said silicon-containing material includes a silicon compound SiOx where about 0.5<x<about 1.5, elemental silicon, or a mixture of thereof.

In some embodiments, the electrochemical device has a charging cut-off voltage of ≥4.45 V.

In some embodiments, the negative electrode of the electrochemical device includes graphite, wherein the weight ratio of the graphite to the silicon-containing material is about 95:5 to about 30:70.

In some embodiments, the negative electrode of the electrochemical device includes graphite, wherein the weight ratio of the graphite to the silicon-containing material is about 95:5 to about 60:40.

In another aspect, the present application provides an electronic device including any electrochemical device as described above.

Additional aspects and advantages of the embodiments of the present application will be described or shown in the following description or interpreted by implementing the embodiments of the present application.

DETAILED DESCRIPTION

The embodiments of the present application will be described in detail below. The embodiments of the present application should not be interpreted as limitations to the protection scope of the present application. Unless otherwise expressly indicated, the following terms used herein have the meanings indicated below.

As used herein, the term "about" is used to describe and explain minor changes. When being used in combination with an event or circumstance, the term may refer to an example in which the event or circumstance occurs precisely, and an example in which the event or circumstance occurs approximately. For example, when being used in combination with a value, the term may refer to a variation range of less than or equal to ±10% of the value, for example, less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. In addition, sometimes, a quantity, a ratio, and another value are presented in a range format in the present application. It should be appreciated that such range formats are for convenience and conciseness, and should be flexibly understood as including not only values explicitly specified to range constraints, but also all individual values or subranges within the ranges, like explicitly specifying each value and each sub-range.

In the detailed description and the claims, a list of items connected by the term "one of" may mean any one of the listed items. For example, if items A and B are listed, then the phrase "one of A and B" means only A or only B. In another example, if items A, B, and C are listed, then the phrase "one of A, B and C" means only A; only B; or only C. The item A may include a single component or multiple components. The item B may include a single component or multiple components. The item C may include a single component or multiple components.

In the detailed description and the claims, a list of items connected by the term "at least one of" or similar terms may mean any combination of the listed items. For example, if items A and B are listed, then the phrase "at least one of A and B" or "at least one of A or B" means only A; only B; or A and B. In another example, if items A, B and C are listed, then the phrase "at least one of A, B and C" "at least one of A, B or C" means only A; or only B; only C; A and B (excluding C); A and C (excluding B); B and C (excluding A); or all of A, B and C. The item A may include a single component or multiple components. The item B may include a single component or multiple components. The item C may include a single component or multiple components.

In the specific embodiment and the claims, in the expression with reference to the number of carbon atoms, i.e. the number after the capital letter "C", such as "$C_1$-$C_{10}$", "$C_3$-$C_{10}$" or the like, the number after "C", for example, "1", "3" or "10", indicate the number of carbon atoms in a specific functional group. That is, the functional groups may include 1-10 carbon atoms and 3-10 carbon atoms, respectively. For example, "$C_1$-$C_4$ alkyl" means an alkyl group having 1-4 carbon atoms, such as $CH_3$—, $CH_3CH_2$—, $CH_3CH_2CH_2$—, $(CH_3)_2CH$—, $CH_3CH_2CH_2CH_2$—, $CH_3CH_2CH(CH_3)$—, or $(CH_3)_3C$—.

As used herein, the term "alkyl group" is intended to be a linear saturated hydrocarbon structure having 1 to 7 carbon atoms. The alkyl group is also intended to be a branched or cyclic hydrocarbon structure having 3 to 7 carbon atoms. For example, the alkyl group may be an alkyl group having 1 to 7 carbon atoms, or an alkyl group having 1 to 4 carbon atoms. When an alkyl group having a specific number of carbon atoms is defined, it is intended to cover all geometric isomers having the carbon number. Therefore, for example, "butyl" means n-butyl, sec-butyl, isobutyl, tert-butyl and cyclobutyl; and "propyl" includes n-propyl, isopropyl and cyclopropyl. Examples of the alkyl group include, but are not limited to, methyl, ethyl, n-propyl, isopropyl, cyclopropyl, n-butyl, isobutyl, sec-butyl, tert-butyl, cyclobutyl, n-pentyl, isoamyl, neopentyl, cyclopentyl, methylcyclopentyl, ethylcyclopentyl, n-hexyl, isohexyl, cyclohexyl, n-heptyl, octyl, cyclopropyl, cyclobutyl, norbornanyl and so on. Additionally, the alkyl group can be optionally substituted.

The term "alkenyl group" refers to a monovalent unsaturated hydrocarbon group which may be straight or branched and which has at least one and usually 1, 2 or 3 carbon-carbon double bonds. Unless otherwise defined, the alkenyl group typically contains from 2 to 7 carbon atoms, for example an alkenyl group having 2 to 7 carbon atoms, or an alkenyl group having 2 to 4 carbon atoms. Representative alkenyl groups include (for example) ethenyl, n-propenyl, iso-propenyl, n-but-2-enyl, butyl-3-enyl, n-hex-3-enyl, and the like. Additionally, the alkenyl group can be optionally substituted.

The term "alkynyl group" refers to a monovalent unsaturated hydrocarbon group which may be straight or branched and which has at least one and usually 1, 2 or 3 carbon-carbon triple bonds. Unless otherwise defined, the alkynyl group is typically an alkynyl group containing from 2 to 7, or from 2 to 4 carbon atoms. Representative alkynyl groups include (for example) ethynyl, prop-2-ynyl (n-propynyl), n-but-2-ynyl, n-hex-3-ynyl and the like. Additionally, the alkynyl group can be optionally substituted.

As used herein, the term "halo" encompasses F, Cl, Br or I.

When the above substituents are substituted, the substituent is selected from the group consisting of halo, and an alkyl group.

As used herein, the content of each component in the electrolyte is based on the total weight of the electrolyte.

I. Electrolyte

In some embodiments, the present application provides an electrolyte including:
 a substituted or unsubstituted thiodilycolic anhydride compound having a structure of Formula I; and
 at least a trinitrile compound having a structure of Formula II or Formula III:

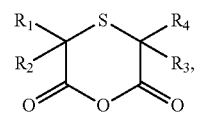

Formula I

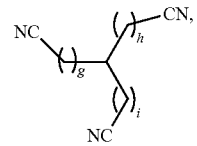

Formula II

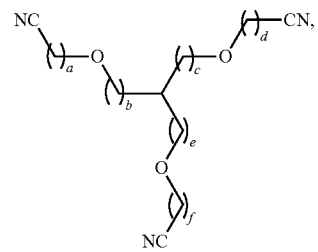

Formula III wherein $R_1$, $R_2$, $R_3$ and $R_4$ are each independently selected from hydrogen, halo, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, substituted or unsubstituted $C_6$-$C_{12}$ aryl, substituted or unsubstituted $C_1$-$C_{10}$ alkoxy, or substituted or unsubstituted $C_6$-$C_{12}$ aryloxy, wherein when substituted, the substituent is halo, cyano, or $C_1$-$C_{10}$ alkyl; and a, d and f are each independently selected from an integer from 1 to 5, and b, c, e, g, h and i are each independently selected from an integer from 0 to 5.

In some embodiments, $R_1$, $R_2$, $R_3$ and $R_4$ are each independently selected from hydrogen, halo, substituted or unsubstituted $C_1$-$C_7$ alkyl, substituted or unsubstituted $C_1$-$C_4$ alkyl, substituted or unsubstituted $C_2$-$C_7$ alkenyl, substituted or unsubstituted $C_2$-$C_4$ alkenyl, substituted or unsubstituted $C_2$-$C_7$ alkynyl, or substituted or unsubstituted $C_2$-$C_4$ alkynyl, wherein when substituted, the substituent is halo or $C_1$-$C_3$ alkyl.

In some embodiments, $R_1$, $R_2$, $R_3$ and $R_4$ are each independently selected from hydrogen, fluoro, $C_1$-$C_7$ alkyl with or without fluoro, $C_1$-$C_4$ alkyl with or without fluoro, $C_2$-$C_7$ alkenyl with or without fluoro, $C_2$-$C_4$ alkenyl with or without fluoro, $C_2$-$C_7$ alkynyl with or without fluoro, or $C_2$-$C_4$ alkynyl with or without fluoro.

In some embodiments, $R_1$, $R_2$, $R_3$, and $R_4$ are each independently selected from hydrogen, fluoro, methyl, ethyl, —$CF_3$, or ethenyl.

In some embodiments, the compound of Formula I includes at least one of:

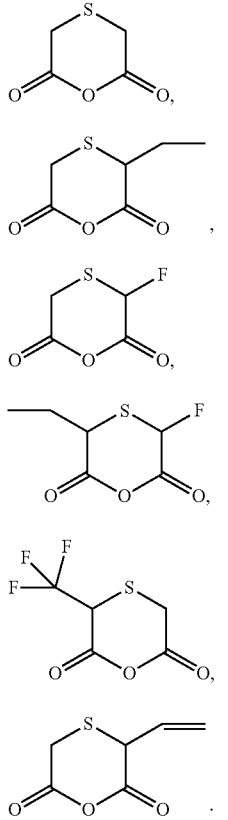

Compound 1

Compound 2

Compound 3

Compound 4

Compound 5

Compound 6

The compound having a structure of Formula II or Formula III includes at least one of:

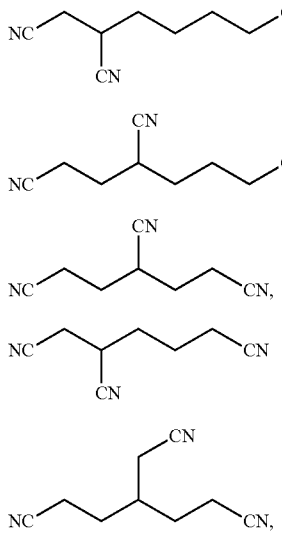

Compound 7

Compound 8

Compound 9

Compound 10

Compound 11

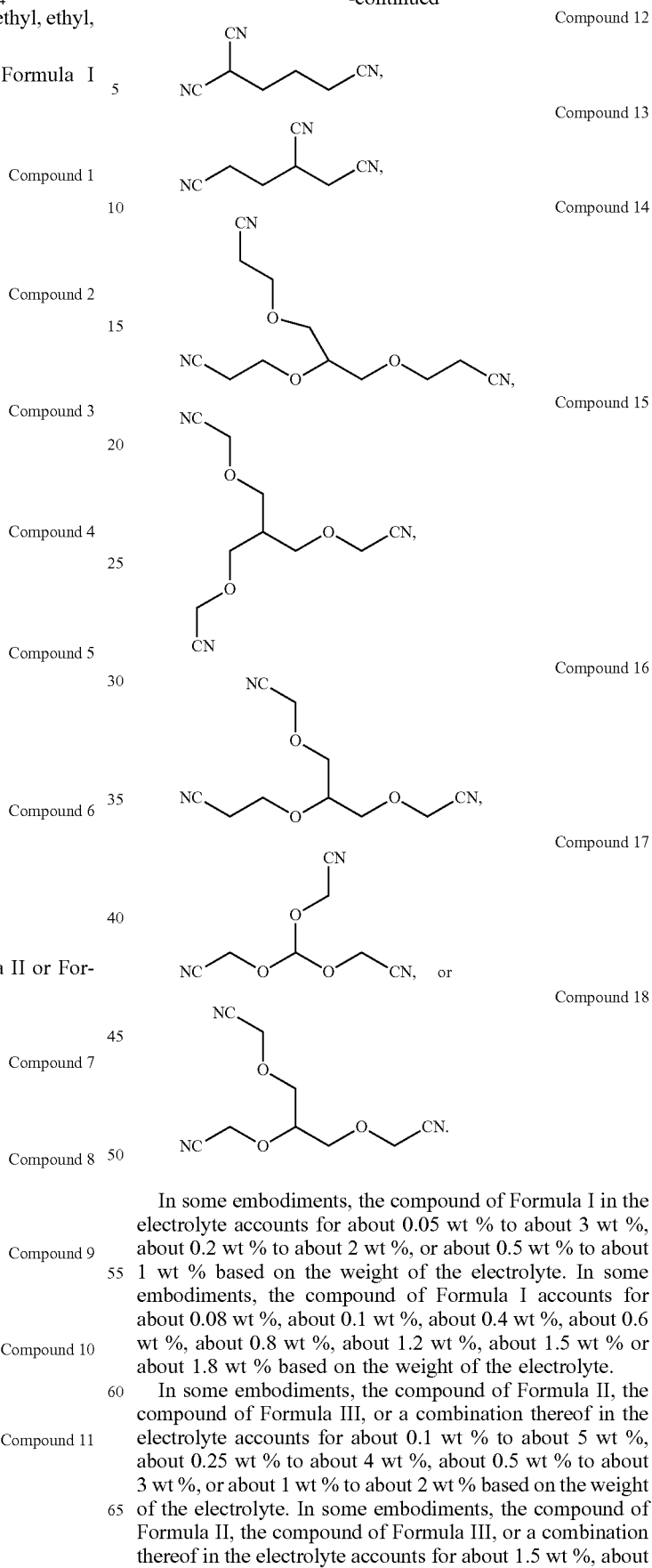

Compound 12

Compound 13

Compound 14

Compound 15

Compound 16

Compound 17 or

Compound 18

In some embodiments, the compound of Formula I in the electrolyte accounts for about 0.05 wt % to about 3 wt %, about 0.2 wt % to about 2 wt %, or about 0.5 wt % to about 1 wt % based on the weight of the electrolyte. In some embodiments, the compound of Formula I accounts for about 0.08 wt %, about 0.1 wt %, about 0.4 wt %, about 0.6 wt %, about 0.8 wt %, about 1.2 wt %, about 1.5 wt % or about 1.8 wt % based on the weight of the electrolyte.

In some embodiments, the compound of Formula II, the compound of Formula III, or a combination thereof in the electrolyte accounts for about 0.1 wt % to about 5 wt %, about 0.25 wt % to about 4 wt %, about 0.5 wt % to about 3 wt %, or about 1 wt % to about 2 wt % based on the weight of the electrolyte. In some embodiments, the compound of Formula II, the compound of Formula III, or a combination thereof in the electrolyte accounts for about 1.5 wt %, about 2 wt %, about 2.5 wt %, about 3 wt %, about 3.5 wt % or about 4.5 wt % based on the weight of the electrolyte.

In some embodiments, the electrolyte further includes an additive A, said additive A includes at least one of the following: lithium difluoro(oxalato)borate (LiDFOB), lithium bis(oxalato)borate (LiBOB), lithium tetrafluoroborate (LiBF$_4$), lithium difluorophosphate (LiPO$_2$F$_2$), lithium tetrafluorophosphate (LiPOF$_4$), lithium tetrafluoro(oxalato) phosphate, lithium difluorobis(oxalato)phosphate, sodium bis(fluorosulfonyl)imide (NaFSI), sodium bis(trifluoromethanesulfonyl)imide (NaTFSI), sodium hexafluorophosphate (NaPF$_6$), potassium bis(fluorosulfonyl)imide (KFSI), potassium bis(trifluoromethanesulfonyl)imide (KTFSI) or potassium hexafluorophosphate (KPF$_6$).

In some embodiments, the additive A accounts for 0 wt % to about 1 wt %, about 0.1 wt % to about 0.9 wt %, about 0.3 wt % to about 0.8 wt %, about 0.4 wt % to about 0.7 wt %, or 0.5 wt % to about 0.6 wt % based on the weight of the electrolyte.

In some embodiments, to further improve the cycle stability of high-energy density lithium batteries, the electrolyte may further include an additive B, wherein the additive B includes at least one of fluoroethylene carbonate (FEC), vinylene carbonate (VC), or 1,3-propane sultone (PS).

In some embodiments, the fluoroethylene carbonate accounts for about 0.01 wt % to about 8 wt %, about 1 wt % to about 7 wt %, about 2 wt % to about 6 wt %, or about 3 wt % to about 5 wt % based on the weight of the electrolyte.

In some embodiments, the vinylene carbonate accounts for about 0.01 wt % to about 2 wt %, about 0.05 wt % to about 0.9 wt %, or about 0.1 wt % to about 0.5 wt % based on the weight of the electrolyte.

In some embodiments, the 1,3-propane sultone accounts for about 0.01 wt % to about 2 wt %, about 0.05 wt % to about 0.9 wt %, or about 0.1 wt % to about 0.5 wt % based on the weight of the electrolyte.

In some embodiments, the additive B accounts for about 0.01 wt % to about 9 wt %, about 1 wt % to about 7 wt %, about 2 wt % to about 6 wt %, or about 3 wt % to about 5 wt % based on the weight of the electrolyte.

In some embodiments, the electrolyte further includes a lithium salt and an organic solvent.

In some embodiments, the lithium salt is one or more selected from an inorganic lithium salt and an organic lithium salt. In some embodiments, the lithium salt includes at least one of a fluorine element, a boron element, and a phosphorus element. In some embodiments, the lithium salt is one or more selected from lithium hexafluorophosphate (LiPF$_6$), lithium bis(trifluoromethanesulphonyl)imide (LiN(CF$_3$SO$_2$)$_2$) (LiTFSI), lithium bis(fluorosulfonyl)imide (Li(N(SO$_2$F)$_2$) (LiFSI), lithium hexafluoroarsenate (LiAsF$_6$), lithium perchlorate (LiClO$_4$), or lithium trifluoromethanesulfonate (LiCF$_3$SO$_3$).

In some embodiments, the content of the lithium salt is about 0.5 M to 1.5 M. In some embodiments, the content of the lithium salt is about 0.8 M to 1.2 M. In some embodiments, the content of the lithium salt is about 1 M to 1.05 M.

The organic solvent includes a cyclic ester and a chain ester. The cyclic ester is at least one selected from ethylene carbonate (EC), propylene carbonate (PC), γ-butyrolactone (BL), and butylene carbonate. The chain ester is at least one selected from dimethyl carbonate (DMC), diethyl carbonate (DEC), ethyl methyl carbonate (EMC), ethyl propyl carbonate, methyl formate (MF), ethyl formate (MA), ethyl acetate (EA), ethyl propionate (EP), propyl propionate (PP), methyl propionate, methyl butyrate, ethyl butyrate, fluorinated ethyl methyl carbonate, fluorinated dimethyl carbonate, fluorinated diethyl carbonate, fluorinated ethyl propionate, fluorinated propyl propionate, fluorinated methyl propionate, fluorinated ethyl acetate, fluorinated methyl acetate, fluorinated propyl acetate, and so on.

In some embodiments, the solvent accounts for about 70 wt % to about 95 wt % based on the weight of the electrolyte.

II. Electrochemical Device

The electrochemical device of the present application includes any device where an electrochemical reaction takes place, and specific examples include all kinds of primary batteries, secondary batteries, fuel cells, solar cells, or capacitors. In particular, the electrochemical device is a lithium secondary battery including a lithium metal secondary battery, a lithium-ion secondary battery, a lithium polymer secondary battery or a lithium-ion polymer secondary battery. In some embodiments, the electrochemical device of the present application is an electrochemical device having a positive electrode having a positive electrode active material capable of absorbing and releasing metal ions; and a negative electrode having a negative electrode active material capable of absorbing and releasing metal ions, and characterized in including any electrolyte of the present application.

Electrolyte

The electrolyte used in the electrochemical device of the present application is any of the aforementioned electrolytes according to the present application. Moreover, the electrolyte used in the electrochemical device of the present application may include other electrolytes falling within the scope of present application.

Negative Electrode

The material used in the negative electrode of the electrochemical device of the present application, and the construction and manufacturing methods therefor are not particularly limited, and may be any of the techniques disclosed in the prior art. In some embodiments, the negative electrode may be one described in U.S. Pat. No. 9,812,739B, which is incorporated herein by reference in its entirety.

In some embodiments, the negative electrode includes a current collector and a negative electrode active material layer on the current collector. The negative electrode active material includes a material that reversibly intercalates/deintercalates lithium ions. In some embodiments, the material that reversibly intercalates/deintercalates lithium ions includes a carbon material. In some embodiments, the carbon material may be any carbon-based negative electrode active material commonly used in lithium-ion rechargeable batteries. In some embodiments, the carbon material includes, but is not limited to, crystalline carbon, amorphous carbon, or a mixture thereof. The crystalline carbon may be formless or plate-shaped, platelet-shaped, spherical or fibrous natural graphite or artificial graphite. The amorphous carbon may be soft carbon, hard carbon, carbonized mesophase pitch, calcined coke, and the like.

In some embodiments, the negative electrode active material layer includes a negative electrode active material. In some embodiments, the negative electrode active material includes, but is not limited to, lithium metal, structured lithium metal, natural graphite, artificial graphite, mesocarbon microbead (MCMB), hard carbon, soft carbon, silicon, silicon-carbon composite, Li—Sn alloy, Li—Sn—O alloy, Sn, SnO, SnO$_2$, lithiated TiO$_2$—Li$_4$Ti$_5$O$_{12}$ having spinel structure, Li—Al alloy and any combination thereof. In some embodiments, the negative electrode active material includes a silicon-containing compound, which includes $SiO_x$ where $0.5<x<1.5$, the elemental silicon, or a mixture of thereof.

When the negative electrode includes a carbon material and a silicon material, based on the total weight of the negative electrode active material, carbon material:silicon material is about 95:5 to about 70:30, about 95:5 to about 60:40, about 95:5 to about 50:50, or about 95:5 to about 40:60, the median particle size D50 of the negative electrode active material is about 0.1 micron to about 100 microns. When the negative electrode includes an alloy material, a negative electrode active material layer can be formed by vapor deposition, sputtering, or plating. When the negative electrode includes lithium metal, a negative electrode active material layer is formed by for example a conductive skeleton of twisted spherical shape and metal particles dispersed in the conductive skeleton. In some embodiments, the conductive skeleton of twisted spherical shape may have a porosity of about 5% to about 85%. In some embodiments, a protective layer may be further disposed on the negative electrode active material layer of lithium metal.

In some embodiments, the negative electrode active material layer includes a binder, and optionally a conductive material. The binder increases the binding of the negative electrode active material particles to each other and the binding of the negative electrode active material to the current collector. In some embodiments, the binder includes, but is not limited to, polyvinyl alcohol, carboxymethyl cellulose, hydroxypropyl cellulose, diacetyl cellulose, polyvinyl chloride, carboxylated polyvinyl chloride, polyvinyl fluoride, a polymer containing ethylene oxide, polyvinylpyrrolidone, polyurethane, polytetrafluoroethylene, poly(1,1-vinylidene fluoride), polyethylene, polypropylene, styrene butadiene rubber, acrylated styrene butadiene rubber, epoxy resins, Nylon and so on.

In some embodiments, the conductive material includes, but is not limited to, a carbon based material, a metal based material, a conductive polymer, or a mixture thereof. In some embodiments, the carbon-based material is selected from natural graphite, artificial graphite, carbon black, acetylene black, ketjen black, carbon fiber, or any combinations thereof. In some embodiments, the metal based material is selected from metal powders, metal fibers, copper, nickel, aluminum, and silver. In some embodiments, the conductive polymer is a polyphenylene derivative.

In some embodiments, the current collector include, but is not limited to, copper foil, nickel foil, stainless steel foil, titanium foil, foamed nickel, foamed copper, polymeric substrates coated with a conductive metal, and any combinations thereof.

The negative electrode can be produced by a production method well known in the art. For example, the negative electrode can be obtained by mixing an active material, a conductive material and a binder in a solvent to prepare an active material composition, and coating the active material composition on a current collector. In some embodiments, the solvent may include, but is not limited to, water.

Positive Electrode

The positive electrode material used in the electrochemical device of the present application can be prepared using materials, construction and manufacturing methods well known in the art. In some embodiments, the positive electrode of the present application can be prepared using the technique described in U.S. Pat. No. 9,812,739B, which is incorporated herein by reference in its entirety.

In some embodiments, the positive electrode includes a current collector and a positive electrode active material layer on the current collector. The positive electrode active material includes at least one lithiated intercalation compound that reversibly intercalates and deintercalates lithium ions. In some embodiments, the positive electrode active material includes a composite oxide. In some embodiments, the composite oxide contains lithium and at least one element selected from the group consisting of cobalt, manganese, and nickel.

In some embodiments, the positive electrode active material is selected from ithium cobaltate ($LiCoO_2$), lithium nickel cobalt manganese (NCM) ternary material, lithium iron phosphate ($LiFePO_4$), lithium manganate ($LiMn_2O_4$) or any combinations thereof.

In some embodiments, the positive electrode active material may have a coating on its surface, or may be mixed with another compound having a coating. The coating may include at least one coating element compound selected from the group consisting of an oxide of a coating element, a hydroxide of a coating element, an oxyhydroxide of a coating element, an oxycarbonate of a coating element, and a hydroxycarbonate of a coating element. The compound used for the coating may be amorphous or crystalline.

In some embodiments, the coating element contained in the coating may include Mg, Al, Co, K, Na, Ca, Si, Ti, V, Sn, Ge, Ga, B, As, Zr or any combinations thereof. The coating can be applied by any method as long as the method does not adversely affect the performance of the positive electrode active material. For example, the method may include any coating method known in the art, such as spraying, dipping, and others.

The positive electrode active material layer further includes a binder, and optionally a conductive material. The binder increases the binding of the positive electrode active material particles to each other and the binding of the positive electrode active material to the current collector.

In some embodiments, the binder includes, but is not limited to, polyvinyl alcohol, hydroxypropyl cellulose, diacetyl cellulose, polyvinyl chloride, carboxylated polyvinyl chloride, polyvinyl fluoride, a polymer containing ethylene oxide, polyvinylpyrrolidone, polyurethane, polytetrafluoroethylene, poly(1,1-vinylidene fluoride), polyethylene, polypropylene, styrene butadiene rubber, acrylated styrene butadiene rubber, epoxy resins, Nylon and so on.

In some embodiments, the conductive material includes, but is not limited to, a carbon based material, a metal based material, a conductive polymer, and a mixture thereof. In some embodiments, the carbon-based material is selected from natural graphite, artificial graphite, carbon black, acetylene black, ketjen black, carbon fiber, or any combinations thereof. In some embodiments, the metal based material is selected from metal powders, metal fibers, copper, nickel, aluminum, and silver. In some embodiments, the conductive polymer is a polyphenylene derivative.

In some embodiments, the current collector may be, but is not limited to, aluminum.

The positive electrode can be prepared by a preparation method well known in the art. For example, the positive electrode can be obtained by mixing an active material, a conductive material and a binder in a solvent to prepare an active material composition, and coating the active material composition on a current collector. In some embodiments, the solvent may include, but is not limited to, N-methylpyrrolidone or the like.

In some embodiments, the positive electrode is prepared by forming a positive electrode material with a positive electrode active material layer including a lithium-transition metal compound powder and a binder on a current collector.

In some embodiments, the positive electrode active material layer can generally be produced by dry mixing a positive electrode material and a binder (and a conductive material and a thickener if needed) to form flakes, and pressing the obtained flakes on a positive electrode current collector; or dissolving or dispersing the material in a liquid medium to form a slurry, coating the slurry on a positive electrode current collector, and drying. In some embodiments, the material of the positive electrode active material layer includes any material known in the art.

Separator Film

In some embodiments, the electrochemical device of the present application is provided with a separator film between the positive electrode and the negative electrode to prevent short circuit. The material and shape of the separator film used in the electrochemical device of the present application are not particularly limited, and may be any of the techniques disclosed in the prior art. In some embodiments, the separator film includes a polymer or an inorganic substance or the like formed of a material which is stable against the electrolyte of the present application.

For example, the separator film may include a substrate layer and a coating. The substrate layer is a non-woven fabric, film, or composite film having a porous structure, and the material of the substrate layer is at least one selected from the group consisting of polyethylene, polypropylene, polyethylene terephthalate, and polyimide. Particularly, a porous polypropylene film, a porous polyethylene film, a polypropylene nonwoven fabric, a polyethylene nonwoven fabric, and a porous polypropylene-polyethylene-polypropylene composite film may be used. One or more substrate layers may be present. When more than one substrate layers are present, the polymers in different substrate layers may have the same or different composition(s), and the weight average molecular weights are different. When more than one substrate layers are present, the shutdown temperature of the polymers in different substrate layers is different.

In some embodiments, to further improve the cycle stability at a high voltage, at least one surface of the substrate layer according to the present application is provided with a coating, which may be a polymer layer or an inorganic layer, or a layer formed by mixing a polymer and an inorganic material. The thickness of the coating is between about 0.1 micron to about 3 microns, about 0.4 micron to about 2.5 microns, about 0.8 micron to about 2 microns, or about 1.2 microns to about 1.5 microns.

The inorganic layer includes a metal oxide $Me_xO_y$, wherein Me is at least one selected from Al, Mg, Zn, Ti or Zr, $1 \leq x \leq 2$, and $1 \leq y \leq 3$. The metal oxide $Me_xO_y$ include one of alumina ($Al_2O_3$), silica, magnesia, titania ($TiO_2$), hafnium dioxide, tin oxide, cerium dioxide, nickel oxide, zinc oxide (ZnO), calcium oxide, zirconia ($ZrO_2$), yttria, silicon carbide, eboehmite, aluminum hydroxide, magnesium hydroxide, calcium hydroxide and barium sulfate, or a combination of more than one thereof. In some embodiments, the metal oxide includes at least one of alumina ($Al_2O_3$), zinc oxide (ZnO), titania ($TiO_2$) or zirconia ($ZrO_2$). The coating further includes a binder. The binder is one selected from the group consisting of polyvinylidene fluoride, a copolymer of vinylidene fluoride-hexafluoropropylene, a polyamide, polyacrylonitrile, a polyacrylate ester, polyacrylic acid, a polyacrylate salt, polyvinylpyrrolidone, polyvinyl ether, polymethyl methacrylate, polytetrafluoroethylene, and polyhexafluoropropylene, or a combination of more than one thereof. The polymer layer contains a polymer, and the material of the polymer includes at least one of the following: a polyamide, polyacrylonitrile, a polyacrylate ester, polyacrylic acid, a polyacrylate salt, polyvinylpyrrolidone, polyvinyl ether, polyvinylidene fluoride or poly(vinylidene fluoride-hexafluoropropylene).

In some embodiments, the ratio of the thickness of the coating to the thickness of the polyolefin layer is about 1:1 to about 1:20, about 1:3 to about 1:18, about 1:5 to about 1:15, or about 1:5 to about 1:12.

III. Application

The electrolyte according to the embodiments of the present application can form a stable SEI protective layer on the surface of the positive electrode and negative electrode material, to ensure that the lithium-ion battery can be stably charged and discharged at a high voltage of ≥4.45V, thus being suitable for use in electronic devices including electrochemical devices.

The use of the electrochemical device according to the present application is not particularly limited, and can be used in various known applications, such as notebook computers, pen-input computers, mobile computers, e-book players, portable phones, portable fax machines, portable copiers, portable printers, head-mounted stereo headphones, video recorders, LCD TVs, portable cleaners, portable CD players, Mini discs, transceivers, electronic notebooks, calculators, memory cards, portable recorders, radios, backup power sources, motors, vehicles, motorcycles, scooters, bicycles, lighting apparatus, toys, game consoles, clocks, electric tools, flashing light, cameras, large batteries for household use, or lithium-ion capacitors.

EXAMPLES

Hereinafter, the present application will be specifically described by way of examples and comparative examples; however, the present application is not limited thereto as long as they do not deviate from the spirit of the present application.

1. Preparation of Lithium-Ion Battery (1) Preparation of Negative Electrode

The negative electrode active material graphite, the binder styrene-butadiene rubber (SBR), and the thickener sodium carboxymethyl cellulose (CMC) were weighed and dispersed in an appropriate amount of water at a weight ratio of 97:2:1, and well mixed with fully stirring. The negative electrode slurry was coated on a 8 micron-thick copper foil as a negative electrode current collector, and then baked at 120° C. for 1 hour. After compacting, cutting, and welding of a lug, the negative electrode was obtained.

(2) Preparation of Positive Electrode

The positive electrode active material lithium cobalt oxide ($LiCoO_2$), conductive carbon, and the binder polyvinylidene fluoride (PVDF) were weighed and dispersed in an appropriate amount of N-methylpyrrolidone (NMP) at a weight ratio of 97:1.5:1.5, and well mixed by stirring. The positive electrode slurry was coated on a 10-micron-thick aluminum foil as a positive electrode current collector, and then baked at 120° C. for 1 hour. After compacting, cutting, and welding of a lug, the positive electrode was obtained.

(3) Preparation of Electrolyte

In a glove box under a dry argon atmosphere, ethylene carbonate (EC), propylene carbonate (PC), diethyl carbonate (DEC), and ethyl propionate (EP) were mixed at a weight ratio of 30:10:30:30. Then $LiPF_6$ was added as a lithium salt. Particular types and amounts of materials were added to the electrolyte (wherein the types and amounts of the added materials are shown in Table 1, and the content of each material was calculated based on the total weight of the electrolyte), and then were well mixed to obtain the electrolyte. The concentration of $LiPF_6$ in the electrolyte was 1.05 mol/L.

(4) Preparation of Separator Film

A 7-micron-thick polyethylene porous separator film was used, and a 1.5-micron-thick coating including $Al_2O_3$ ceramic and a polymer was applied to one side of the separator film.

(5) Preparation of Lithium-Ion Battery

The positive electrode, the separator film, and the negative electrode were positioned in order such that the separator film was placed between the positive electrode and the negative electrode, then they were wound, welded with lugs, placed in an aluminum foil packaging bag, and baked at 80° C. to remove water. The electrolyte was injected. After sealing, formation, venting, and capacity test, a lithium-ion secondary battery was obtained. The size of the obtained lithium-ion battery was 3.3 mm×39 mm×96 mm.

Examples 1 to 21 and Comparative Examples 1 to 4

The electrolytes and lithium-ion batteries of Examples 1 to 21 and Comparative Examples 1 to 4 were prepared following the methods as described in (1) to (5) above.

Example 22

The electrolyte and lithium-ion battery of Example 22 were prepared, wherein the negative electrode was prepared following the method described below, and the others were prepared according to the methods as described in (2) to (5) above.

The negative electrode active material graphite, the negative electrode active material SiO, the binder styrene-butadiene rubber (SBR), and the thickener sodium carboxymethyl cellulose (CMC) were weighed and dispersed in an appropriate amount of water at a weight ratio of 87:10:2:1, and well mixed by stirring. The negative electrode slurry was coated on an 8-micron-thick copper foil which is used as a negative electrode current collector, and then baked at 120° C. for 1 hour. After compacting, cutting, and welding of a lug, the negative electrode was obtained.

The same positive electrode was used. Because the capacity per gram of graphite active material is much lower than the SiO material, when the SiO material is used as the negative electrode material, the load of the negative electrode will be lower than that of Example 1, so that the thickness of the negative electrode will be reduced, and the battery will be thinner

TABLE 1

| | Examples and comparative examples | | | | | |
|---|---|---|---|---|---|---|
| | Additive (wt %) | | | | | |
| | Compound of Formula I | | | | Formula II or Formula III Compound | |
| Examples | Compound 1 | Compound 2 | Compound 3 | Compound 5 | Compound 8 | Compound 14 |
| Example 1 | 1 | / | / | / | 2 | / |
| Example 2 | 0.2 | / | / | / | 2 | / |
| Example 3 | 0.5 | / | / | / | 2 | / |
| Example 4 | 2 | / | / | / | 2 | / |
| Example 5 | 3 | / | / | / | 2 | / |
| Example 6 | / | 1 | / | / | 2 | / |
| Example 7 | / | / | 1 | / | 2 | / |
| Example 8 | / | / | / | 1 | 2 | / |
| Example 9 | 1 | / | / | / | 0.5 | / |
| Example 10 | 1 | / | / | / | 1 | / |
| Example 11 | 1 | / | / | / | 3 | / |
| Example 12 | 1 | / | / | / | 5 | / |
| Example 13 | 1 | / | / | / | / | 2 |
| Example 14 | 1 | / | / | / | 2 | / |
| Example 15 | 1 | / | / | / | 2 | / |
| Example 16 | 1 | / | / | / | 2 | / |
| Example 17 | 1 | / | / | / | 2 | / |
| Example 18 | 1 | / | / | / | 2 | / |
| Example 19 | 1 | / | / | / | 2 | / |
| Example 20 | 1 | / | / | / | 2 | / |
| Example 21 | 1 | / | / | / | 2 | / |
| Example 22 | 1 | / | / | / | 2 | / |
| Comparative Example 1 | / | / | / | / | 2 | / |
| Comparative Example 2 | 1 | / | / | / | / | / |
| Comparative Example 3 | / | / | / | / | 2 | / |
| Comparative Example 4 | 1 | / | / | / | / | / |

TABLE 1-continued

| | Examples | Additive (wt %) | | | | | negative electrode active material |
|---|---|---|---|---|---|---|---|
| | | Additive A | | | Additive B | | |
| | | LiDFOB | LiPO$_2$F$_2$ | NaPF$_6$ | FEC | PS | |
| | Example 1 | / | / | / | / | / | Graphite |
| | Example 2 | / | / | / | / | / | Graphite |
| | Example 3 | / | / | / | / | / | Graphite |
| | Example 4 | / | / | / | / | / | Graphite |
| | Example 5 | / | / | / | / | / | Graphite |
| | Example 6 | / | / | / | / | / | Graphite |
| | Example 7 | / | / | / | / | / | Graphite |
| | Example 8 | / | / | / | / | / | Graphite |
| | Example 9 | / | / | / | / | / | Graphite |
| | Example 10 | / | / | / | / | / | Graphite |
| | Example 11 | / | / | / | / | / | Graphite |
| | Example 12 | / | / | / | / | / | Graphite |
| | Example 13 | / | / | / | / | / | Graphite |
| | Example 14 | 0.5 | / | / | / | / | Graphite |
| | Example 15 | / | 0.5 | / | / | / | Graphite |
| | Example 16 | / | 0.1 | / | / | / | Graphite |
| | Example 17 | / | / | 0.1 | / | / | Graphite |
| | Example 18 | / | / | / | 3 | / | Graphite |
| | Example 19 | / | / | / | / | 2 | Graphite |
| | Example 20 | / | / | / | 3 | 2 | Graphite |
| | Example 21 | 0.5 | / | / | 3 | 2 | Graphite |
| | Example 22 | / | / | / | / | / | Graphite + SiO |
| | Comparative Example 1 | / | / | / | / | / | Graphite |
| | Comparative Example 2 | / | / | / | / | / | Graphite |
| | Comparative Example 3 | / | / | / | 3 | 2 | Graphite |
| | Comparative Example 4 | / | / | / | 3 | 2 | Graphite |

"/" denotes that the substance is not present.

2. Cycle Performance Test of Lithium-Ion Battery (1) Intermittent Cycle Test at 45° C.

At 45° C., the battery was charged to 4.45V at a constant current of 0.5 C, and then was charged at a constant voltage to a cutoff current of 0.05 C. The battery was allowed to stand for 20 hours at 45° C.; and then discharged to 3.0V at a constant current of 0.5 C. The process was repeated 100 times, and the capacity retention rate of the battery was recorded.

Capacity retention rate after the Nth cycle of the battery=discharge capacity during the Nth cycle of the battery/initial discharge capacity of the battery×100%

(2) Gas Production Test of Battery During High-Temperature Storage after Over-Discharge At 25° C., the lithium-ion battery was charged at a constant current of 0.5 C to a voltage of 4.45V and then charged at a constant voltage of 4.45V until the current is 0.05 C; after standing for 5 minutes, the battery was discharged at a constant current of 0.5 C to a voltage of 3.0V and then was discharged at a constant current of 0.05 C to a voltage of 1.5V. After the discharge is completed, the battery was placed in an oven at 60° C., the thickness of the soft-pack battery was tested every 3 days, and the thickness expansion rate of the lithium-ion battery was recorded.

Thickness expansion rate (%) of lithium-ion battery after storage for $X$ days=(battery thickness on day $X$ after storage/battery thickness after over discharge−1)×100%.

(3) Energy Density of Lithium-Ion Battery

Battery size test: Three batteries from Example 1 were taken, charged to 3.9V at 25° C. at a constant current of 0.5 C, and then charged at a constant voltage to a cutoff current of 0.05 C. The battery thickness, width, and length were measured use a micrometer.

At 25° C., the battery was charged to 4.45V at a constant current of 0.5 C, and then charged at a constant voltage to a cutoff current of 0.025 C. The battery was then allowed to stand for 5 minutes; and discharged to 3.0V at a constant current of 0.1 C. The discharge energy of the lithium-ion battery was recorded.

Energy density (Wh/L)=discharge energy (Wh)/(battery thickness (mm)×battery width (mm)×battery length (mm)×10$^{-6}$)

A. The electrolytes and lithium-ion batteries of Examples 1 to 20 and Comparative Examples 1 to 4 were prepared following the methods as described above. The intermittent cycle performance of lithium-ion batteries and the thickness expansion rate of the batteries after storage at 60° C. and 1.5V were tested. The test results are shown in Tables 2 and 3.

TABLE 2

Intermittent cycle performance of lithium-ion batteries

Capacity retention rate after intermittent cycles at 45° C., %

| Examples | 20 cycles | 40 cycles | 60 cycles | 80 cycles | 100 cycles |
|---|---|---|---|---|---|
| Example 1 | 93.58 | 89.36 | 83.27 | 78.55 | 71.43 |
| Example 2 | 92.74 | 88.19 | 82.25 | 77.02 | 68.32 |
| Example 3 | 93.20 | 88.65 | 82.59 | 77.84 | 69.50 |
| Example 4 | 93.78 | 89.67 | 83.86 | 79.03 | 72.55 |
| Example 5 | 92.76 | 88.42 | 82.49 | 77.63 | 68.95 |
| Example 6 | 93.41 | 88.68 | 82.54 | 77.23 | 69.55 |
| Example 7 | 92.76 | 88.43 | 82.36 | 77.27 | 68.83 |
| Example 8 | 92.65 | 87.72 | 81.84 | 76.64 | 68.17 |
| Example 9 | 92.52 | 87.58 | 81.60 | 75.98 | 66.30 |
| Example 10 | 92.64 | 88.42 | 82.65 | 77.83 | 70.45 |
| Example 11 | 94.16 | 90.25 | 83.80 | 79.04 | 71.93 |
| Example 12 | 93.30 | 89.09 | 83.02 | 78.31 | 71.22 |
| Example 13 | 93.24 | 89.00 | 82.97 | 78.45 | 71.16 |
| Example 14 | 94.04 | 89.59 | 83.85 | 79.04 | 72.13 |
| Example 15 | 93.85 | 89.43 | 83.59 | 78.94 | 72.19 |
| Example 16 | 93.62 | 89.40 | 83.32 | 78.72 | 71.65 |
| Example 17 | 93.66 | 89.43 | 83.42 | 78.79 | 71.82 |
| Example 18 | 94.22 | 90.28 | 83.90 | 79.35 | 72.54 |
| Example 19 | 94.38 | 90.70 | 84.32 | 79.80 | 72.88 |
| Example 20 | 95.18 | 91.38 | 85.27 | 80.66 | 73.72 |
| Example 21 | 95.23 | 91.47 | 85.64 | 81.42 | 74.56 |
| Example 22 | 92.32 | 86.53 | 81.04 | 75.26 | 65.88 |
| Comparative Example 1 | 91.37 | 86.46 | 78.77 | 69.19 | 58.22 |
| Comparative Example 2 | 89.63 | 84.68 | 74.62 | 61.41 | 42.37 |
| Comparative Example 3 | 91.36 | 87.24 | 78.47 | 69.47 | 59.08 |
| Comparative Example 4 | 90.35 | 85.84 | 76.74 | 64.16 | 45.66 |

TABLE 3

Thickness expansion of battery after storage at 60° C. and 1.5 V

Thickness expansion rate of batteries after storage at 1.5 V and 60° C., %

| Examples | 4 days | 8 days | 12 days | 16 days | 20 days |
|---|---|---|---|---|---|
| Example 1 | 0.57 | 1.46 | 3.55 | 4.77 | 6.26 |
| Example 2 | 0.88 | 1.89 | 4.54 | 6.18 | 8.42 |
| Example 3 | 0.64 | 1.60 | 3.85 | 5.56 | 7.14 |
| Example 4 | 0.46 | 1.22 | 2.84 | 3.63 | 5.38 |
| Example 5 | 0.41 | 0.98 | 2.16 | 3.08 | 4.72 |
| Example 6 | 0.61 | 1.52 | 3.66 | 4.86 | 6.93 |
| Example 7 | 0.68 | 1.63 | 3.89 | 5.32 | 7.62 |
| Example 8 | 0.64 | 1.59 | 3.75 | 5.10 | 7.24 |
| Example 9 | 0.62 | 1.55 | 3.68 | 4.97 | 6.97 |
| Example 10 | 0.60 | 1.48 | 3.64 | 4.88 | 6.49 |
| Example 11 | 0.54 | 1.41 | 3.48 | 4.54 | 6.03 |
| Example 12 | 0.50 | 1.39 | 3.27 | 4.29 | 5.86 |
| Example 13 | 0.58 | 1.49 | 3.58 | 4.78 | 6.32 |
| Example 14 | 0.54 | 1.26 | 3.33 | 4.27 | 5.78 |
| Example 15 | 0.52 | 1.23 | 3.23 | 4.06 | 5.57 |
| Example 16 | 0.55 | 1.38 | 3.42 | 4.55 | 6.08 |
| Example 17 | 0.59 | 1.52 | 3.67 | 5.03 | 6.58 |
| Example 18 | 0.65 | 1.63 | 3.84 | 5.11 | 6.64 |
| Example 19 | 0.55 | 1.37 | 3.28 | 4.28 | 5.53 |
| Example 20 | 0.56 | 1.40 | 3.52 | 4.65 | 6.09 |
| Example 21 | 0.51 | 1.29 | 3.44 | 4.36 | 5.65 |
| Example 22 | 0.70 | 1.63 | 4.75 | 6.39 | 9.17 |
| Comparative Example 1 | 1.87 | 5.58 | 28.38 | 55.72 | 86.56 |
| Comparative Example 2 | 1.25 | 3.48 | 6.83 | 34.25 | 63.29 |
| Comparative Example 3 | 1.68 | 4.96 | 8.75 | 42.33 | 76.54 |
| Comparative Example 4 | 0.95 | 2.76 | 5.54 | 9.27 | 36.27 |

It can be seen from the test results of Example 1 and Comparative Examples 1 and 2 that the addition of the compounds of Formula I (e.g., Compound 1) and Formula II (e.g., Compound 8) to the electrolyte can significantly improve the capacity retention rate of lithium-ion batteries after intermittent cycles at high temperature; and after over-discharge to 1.5V, no obvious bulging occurs after storage at 60° C. for 20 days, and the thickness expansion rate of the battery is <20%.

According to the test results of Examples 1 to 5 and Comparative Example 1, it can be known that addition of a suitable amount of the compound of Formula II (e.g., Compound 8) as well as the compound of Formula I (e.g., Compound 1) in the range of about 0.05 wt % to about 3 wt % to the electrolyte can significantly improve the capacity retention rate of lithium-ion batteries at high temperature and the high-temperature storage performance after over-discharge of the battery. When the compound of Formula I accounts for preferably about 0.5 wt % to about 2 wt % based on the weight of the electrolyte, the effect is particularly desirable.

According to the test results of Example 1 and Examples 6 to 8, it can be seen that when each example of the compounds of Formula I (e.g., Compound 1, Compound 2, Compound 3, or Compound 5) is added to the electrolyte in combination with the compound of Formula II (e.g., Compound 8), similar technical effects can be obtained.

According to the test results of Example 1, Examples 9 to 12 and Comparative Example 2, it can be seen that the addition of a suitable amount of the compound of Formula I (e.g., Compound 1) as well as the compound of Formula II (e.g., Compound 8) in the range of about 0.1 wt % to about 5 wt % to the electrolyte can significantly improve the capacity retention rate of lithium-ion batteries at high temperature and the high-temperature storage performance after over-discharge of the battery. When the compound of Formula II accounts for preferably about 2 to about 5 wt % based on the weight of the electrolyte, the effect is particularly desirable.

According to the test results of Example 1 and Example 13, it can be seen that when the compound of Formula II (e.g., Compound 8) or the compound of Formula III (e.g., Compound 14) is added to the electrolyte in combination with the compound of Formula I (e.g., Compound 1), similar technical effects can be obtained.

According to the test results of Example 1, Examples 14 to 21 and Comparative Examples 1 to 4, it can be seen that when the electrolyte with the compound of Formula I (e.g., Compound 1) and the compound of Formula II (e.g., Compound 8) is further added with an appropriate amount of LiDFOB, LiPO$_2$F$_2$, NaPF$_6$, FEC or PS, the performance of the battery can be further improved, the capacity retention rate after intermittent cycles and the suppression of gas production during high-temperature storage at 1.5V are both further improved.

B. The electrolytes and lithium-ion batteries of Examples 1 and 22 were prepared according to the above preparation method. The energy density of lithium-ion batteries, and the intermittent cycle performance and the thickness expansion rate of the batteries after storage at 60° C. and 1.5V were tested. The test results are shown in Tables 4 and 6.

TABLE 4

Energy density of batteries with various negative electrodes

| Examples | Battery No. | Discharge capacity Wh | Battery thickness mm | Battery width mm | Battery length mm | Energy density Wh/L |
|---|---|---|---|---|---|---|
| Example 1 | 1# | 8.372 | 3.423 | 38.96 | 95.31 | 658.67 |
| | 2# | 8.369 | 3.389 | 39.02 | 95.34 | 663.80 |
| | 3# | 8.381 | 3.412 | 39.04 | 95.29 | 660.28 |
| | Mean | 8.374 | 3.408 | 39.007 | 95.313 | 660.92 |
| Example 22 | 1# | 8.225 | 3.223 | 38.537 | 95.282 | 695.00 |
| | 2# | 8.226 | 3.237 | 38.571 | 95.360 | 690.91 |
| | 3# | 8.221 | 3.229 | 38.623 | 95.327 | 691.50 |
| | Mean | 8.224 | 3.230 | 38.577 | 95.323 | 692.47 |

TABLE 5

Intermittent cycle performance of lithium-ion batteries with various negative electrodes

| | Capacity retention rate after intermittent cycles at 45° C., % | | | | |
|---|---|---|---|---|---|
| Examples | 20 cycles | 40 cycles | 60 cycles | 80 cycles | 100 cycles |
| Example 1 | 93.58 | 89.36 | 83.27 | 78.55 | 71.43 |
| Example 22 | 92.32 | 86.53 | 81.04 | 75.26 | 65.88 |

TABLE 6

Thickness expansion of lithium-ion batteries with various negative electrodes after storage at 60° C. and 1.5 V

| | Thickness expansion rate of batteries after storage at 1.5 V and 60° C., % | | | | |
|---|---|---|---|---|---|
| Examples | 4 days | 8 days | 12 days | 16 days | 20 days |
| Example 1 | 0.57 | 1.46 | 3.55 | 4.77 | 6.26 |
| Example 22 | 0.70 | 1.63 | 4.75 | 6.39 | 9.17 |

In Example 22, a negative electrode containing graphite and a SiO material is used, and in Example 1, a graphite negative electrode is used. The positive electrode materials in the two examples are the same. The capacity per gram of the graphite negative electrode is far lower than that of the SiO material. Therefore, the load in Example 22 (wherein the negative electrode contains graphite and SiO material) is lower than that in Example 1 (wherein the negative electrode contains graphite). The battery obtained in Example 22 is smaller in volume and higher in energy density than Example 1.

Based on the experimental results of Example 1 and Example 22, it can be seen that both a lithium-ion battery having a graphite negative electrode and a lithium-ion battery having a SiO negative electrode can achieve obviously improved intermittent cycle performance and storage performance at 60° C. and 1.5V as long as the electrolyte of the present application is used therein. The improvement for lithium batteries having a graphite negative electrode is particularly significant.

In summary, the electrolyte provided in the present application can form a stable SEI protective layer on the surface of the positive electrode and negative electrode materials, so as to allow the lithium-ion battery to be stably charged and discharged at a high voltage of ≥4.45V. The lithium ion secondary batteries provided in the present application work well at a high energy density and a charging cut-off voltage of ≥4.45V, and the lithium-ion battery has excellent high-temperature intermittent cycle performance, and excellent high-temperature resistance in a discharge state.

The foregoing descriptions are merely a few embodiments of the present invention and are not intended to limit the present invention in any manner. Although the present invention is described with reference to preferred embodiments, the embodiments are not intended to limit the present invention. A person skilled in the art may make some changes or modifications using the technical contents disclosed above without departing from the scope of the technical solutions of the present invention, and such changes and modifications are equivalent to equivalent implementation cases and shall fall within the scope of the technical solutions.

Throughout the specification, references to "embodiment", "part of embodiments", "one embodiment", "another example", "example", "specific example" or "part of examples" mean that at least one embodiment or example of the present application includes specific features, structures, materials or characteristics described in the embodiment or example. Therefore, the descriptions appear throughout the specification, such as "in some embodiments," "in an embodiment," "in one embodiment," "in another example," "in an example," "in a particular example" or "for example," are not necessarily the same embodiment or example in the application. Furthermore, the specific features, structures, materials or characteristics in the descriptions can be combined in any suitable manner in one or more embodiments or examples. Although the illustrative embodiments have been shown and described, it should be understood by those skilled in the art that the above embodiments cannot be interpreted as limitations to the present application, and the embodiments can be changed, substituted and modified without departing from the spirit, principle and scope of the present application.

What is claimed is:

1. An electrolyte, comprising:

a compound of Formula I, and at least one of a compound of Formula II or a compound of Formula III,

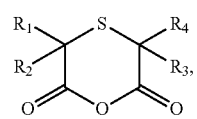

Formula I

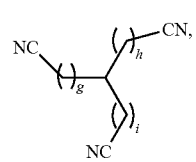

Formula II

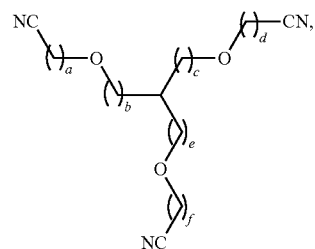

Formula III wherein $R_1$, $R_2$, $R_3$ and $R_4$ are each independently selected from hydrogen, fluoro, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, substituted or unsubstituted $C_6$-$C_{12}$ aryl, substituted or unsubstituted $C_1$-$C_{10}$ alkoxy, or substituted or unsubstituted $C_6$-$C_{12}$ aryloxy, wherein when substituted, the substituent is fluoro, cyano or $C_1$-$C_{10}$ alkyl; and a, d and f are each independently selected from an integer from 1 to 5, and b, c, e, g, h and i are each independently selected from an integer from 0 to 5.

2. The electrolyte according to claim 1, wherein the compound of Formula I comprises at least one of:

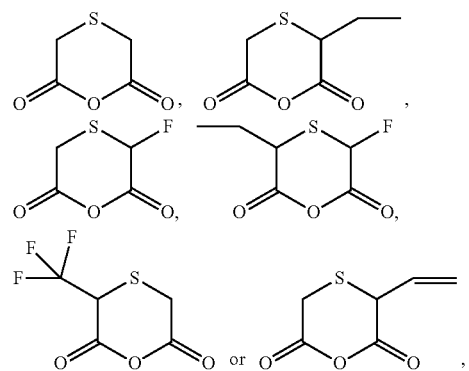

wherein the compound of Formula I is 0.05 wt % to 3 wt % of the weight of the electrolyte.

3. The electrolyte according to claim 1, wherein the compound of Formula II and the compound of Formula III comprise at least one of

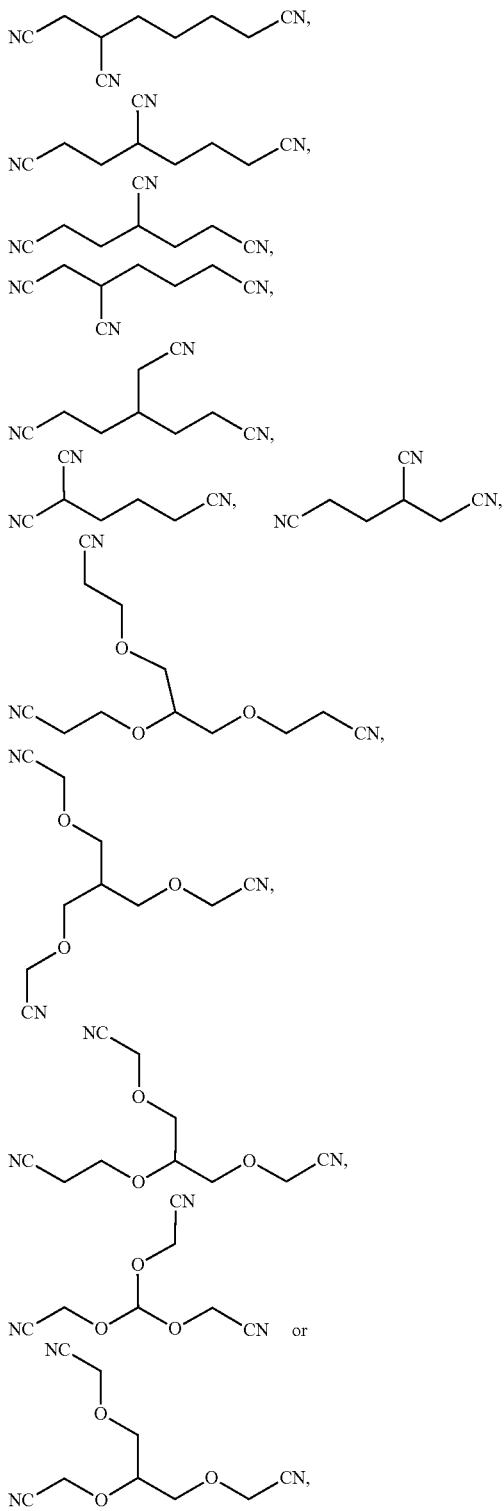

and
the compound of Formula II, the compound of Formula III or a combination thereof is 0.1 wt % to 5 wt % based of the weight of the electrolyte.

4. The electrolyte according to claim 1, further comprising an additive, the additive includes at least one of the following: lithium difluoro(oxalato)borate, lithium bis(oxalato)borate, lithium tetrafluoroborate, lithium difluorophosphate, lithium tetrafluorophosphate, lithium tetrafluoro(oxalato)phosphate, lithium difluorobis(oxalato)phosphate, sodium bis(fluorosulfonyl)imide, sodium bis(trifluoromethanesulfonyl)imide, sodium hexafluorophosphate, potassium bis(fluorosulfonyl)imide, potassium bis(trifluoromethanesulfonyl)imide, or potassium hexafluorophosphate, wherein the additive is ≤1 wt % of the weight of the electrolyte.

5. An electrochemical device, comprising: a positive electrode, a negative electrode, a separator film, and an electrolyte
wherein the electrolyte comprises
a compound of Formula I, and
at least one of a compound of Formula II or a compound of Formula III,

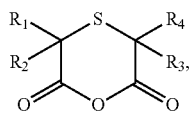

Formula I

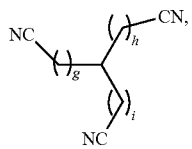

Formula II

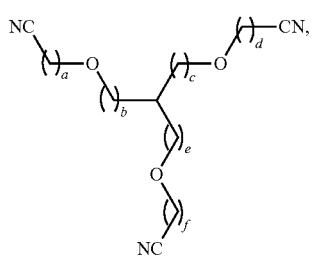

Formula III wherein $R_1$, $R_2$, $R_3$ and $R_4$ are each independently selected from hydrogen, fluoro, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, substituted or unsubstituted $C_6$-$C_{12}$ aryl, substituted or unsubstituted $C_1$-$C_{10}$ alkoxy, or substituted or unsubstituted $C_6$-$C_{12}$ aryloxy, wherein when substituted, the substituent is fluoro, cyano or $C_1$-$C_{10}$ alkyl; and a, d and f are each independently selected from an integer from 1 to 5, and b, c, e, g, h and i are each independently selected from an integer from 0 to 5.

6. The electrochemical device according to claim 5, wherein the separator film comprises a polyolefin layer with a coating on the surface, wherein the coating comprises a metal oxide $Me_xO_y$, wherein Me is at least one selected from Al, Mg, Zn, Ti or Zr, $1 \leq x \leq 2$, and $1 \leq y \leq 3$; the thickness of the coating is 0.1 micron to 3 microns; and a ratio of the thickness of the coating to the thickness of the polyolefin layer is 1:1 to 1:20.

7. The electrochemical device according to claim 6, wherein the metal oxide includes at least one of $Al_2O_3$, ZnO, $SiO_2$, MgO, $TiO_2$ or $ZrO_2$.

8. The electrochemical device according to claim 5, wherein the negative electrode comprises $SiO_x$ where $0.5<x<1.5$, elemental silicon, or a mixture of thereof.

9. The electrochemical device according to claim 5, wherein the electrochemical device has a charging cut-off voltage of $\geq 4.45V$.

10. The electrochemical device according to claim 5, wherein the compound of Formula I comprises at least one of:

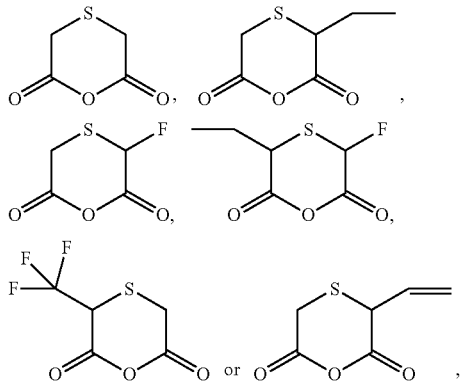

wherein the compound of Formula I accounts for 0.05 wt % to 3 wt % based on the weight of the electrolyte.

11. The electrochemical device according to claim 5, wherein the compound of Formula II and the compound of Formula III comprise at least one of

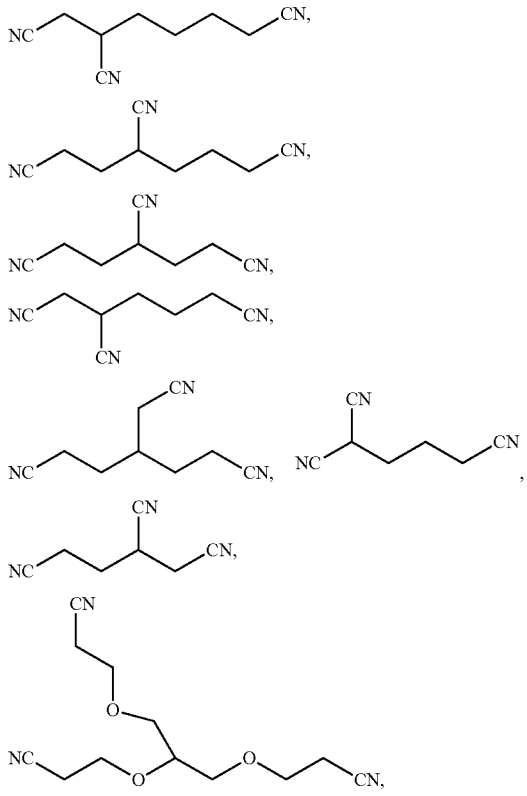

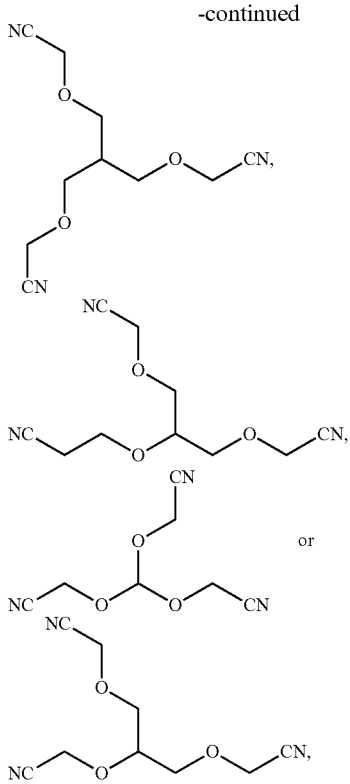

and the compound of Formula II, the compound of Formula III or a combination thereof accounts for 0.1 wt % to 5 wt % based on the weight of the electrolyte.

12. The electrochemical device according to claim 5, wherein the electrolyte further comprises an additive, the additive includes at least one of the following: lithium difluoro(oxalato)borate, lithium bis(oxalato)borate, lithium tetrafluoroborate, lithium difluorophosphate, lithium tetrafluorophosphate, lithium tetrafluoro(oxalato)phosphate, lithium difluorobis(oxalato)phosphate, sodium bis(fluorosulfonyl)imide, sodium bis(trifluoromethanesulfonyl)imide, sodium hexafluorophosphate, potassium bis(fluorosulfonyl)imide, potassium bis(trifluoromethanesulfonyl)imide, or potassium hexafluorophosphate, wherein the additive is $\leq 1$ wt % of the weight of the electrolyte.

13. The electrochemical device according to claim 10, wherein the separator film comprises a polyolefin layer with a coating on the surface, wherein the coating comprises a metal oxide $Me_xO_y$, wherein Me is at least one selected from Al, Mg, Zn, Ti or Zr, $1\leq x\leq 2$, and $1\leq y\leq 3$; the thickness of the coating is 0.1 micron to 3 microns; and a ratio of the thickness of the coating to the thickness of the polyolefin layer is 1:1 to 1:20.

14. The electrochemical device according to claim 13, wherein the metal oxide includes at least one of $Al_2O_3$, ZnO, $SiO_2$, MgO, $TiO_2$ or $ZrO_2$.

15. The electrochemical device according to claim 12, wherein the negative electrode comprises $SiO_x$ where $0.5<x<1.5$, elemental silicon, or a mixture thereof.

16. The electrochemical device according to claim 12, wherein the electrochemical device has a charging cut-off voltage of $\geq 4.45V$.

17. An electronic device, comprising an electrochemical device, wherein the electrochemical device comprises a positive electrode, a negative electrode, a separator film, and an electrolyte;

wherein, the electrolyte comprises
a compound of Formula I, and
at least one of a compound of Formula II or a compound of Formula III,

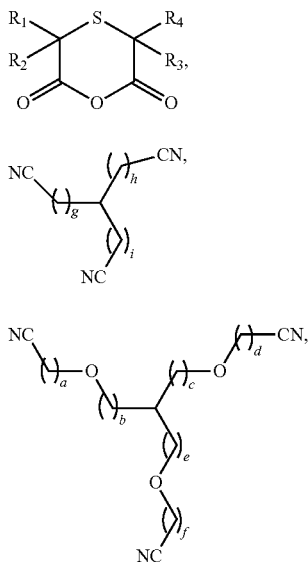

Formula I

Formula II

Formula III wherein $R_1$, $R_2$, $R_3$ and $R_4$ are each independently selected from hydrogen, fluoro, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, substituted or unsubstituted $C_6$-$C_{12}$ aryl, substituted or unsubstituted $C_1$-$C_{10}$ alkoxy, or substituted or unsubstituted $C_6$-$C_{12}$ aryloxy, wherein when substituted, the substituent is fluoro, cyano or $C_1$-$C_{10}$ alkyl; and a, d and f are each independently selected from an integer from 1 to 5, and b, c, e, g, h and i are each independently selected from an integer from 0 to 5.

18. The electronic device according to claim 17, wherein the compound of Formula I comprises at least one of:

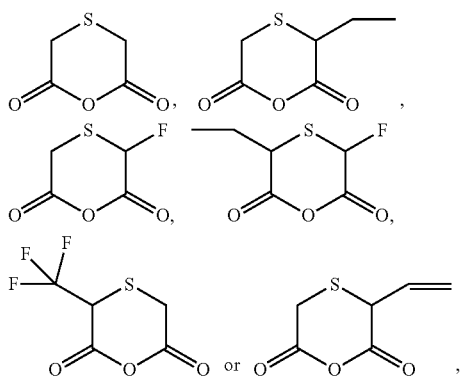

wherein the compound of Formula I accounts for 0.05 wt % to 3 wt % based on the weight of the electrolyte.

19. The electronic device according to claim 17, wherein the compound of Formula II and the compound of Formula III comprise at least one of

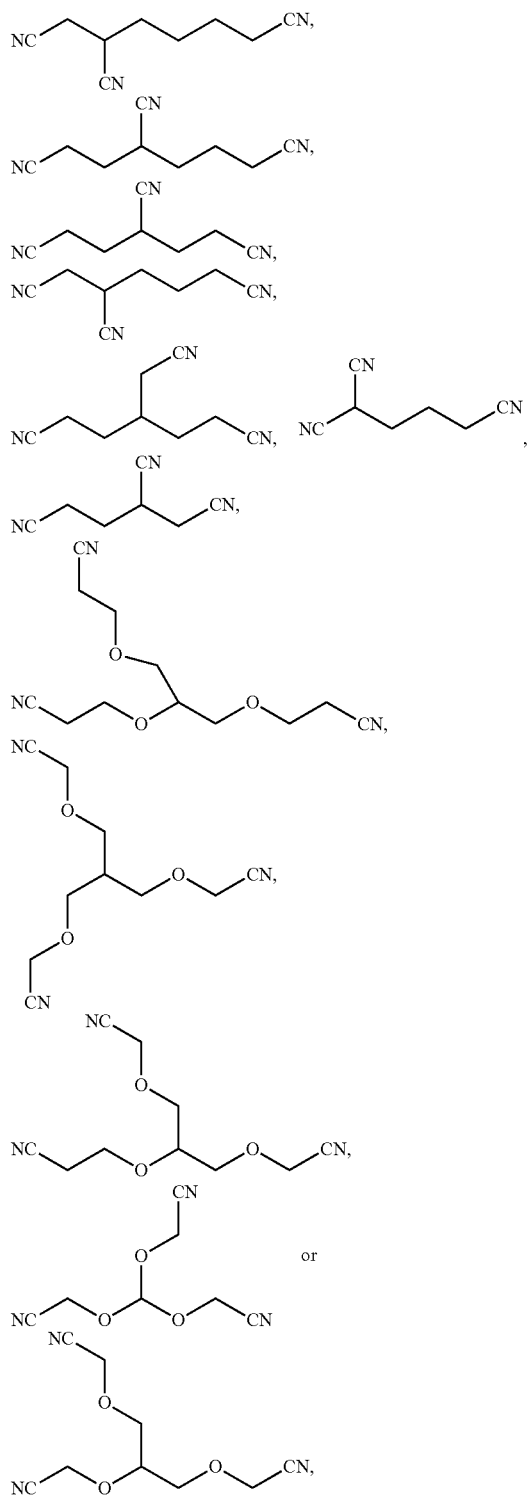

and the compound of Formula II, the compound of Formula III or a combination thereof is 0.1 wt % to 5 wt % of the weight of the electrolyte.

20. The electronic device according to claim 17, wherein the electrolyte further comprises an additive, the additive includes at least one of the following: lithium difluoro (oxalato)borate, lithium bis(oxalato)borate, lithium tetrafluoroborate, lithium difluorophosphate, lithium tetrafluorophosphate, lithium tetrafluoro(oxalato)phosphate, lithium difluorobis(oxalato)phosphate, sodium bis(fluorosulfonyl)imide, sodium bis(trifluoromethanesulfonyl)imide, sodium hexafluorophosphate, potassium bis(fluorosulfonyl)imide, potassium bis(trifluoromethanesulfonyl)imide, or potassium hexafluorophosphate, wherein the additive is ≤1 wt % of the weight of the electrolyte.

* * * * *